US010697870B2

United States Patent
Urano et al.

(10) Patent No.: US 10,697,870 B2
(45) Date of Patent: Jun. 30, 2020

(54) BLOOD TEST KIT AND ANALYZING METHOD USING THE SAME

(71) Applicant: FUJIFILM Corporation, Tokyo (JP)

(72) Inventors: Hikaru Urano, Ashigarakami-gun (JP); Tatsuya Ishizaka, Ashigarakami-gun (JP); Haruyasu Nakatsugawa, Ashigarakami-gun (JP); Susumu Osawa, Tokyo (JP); Shinya Sugimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 15/861,238

(22) Filed: Jan. 3, 2018

(65) Prior Publication Data

US 2018/0143116 A1    May 24, 2018

Related U.S. Application Data

(63) Continuation of application No. PCT/JP2016/070008, filed on Jul. 6, 2016.

(30) Foreign Application Priority Data

Jul. 6, 2015  (JP) .................................. 2015-135066
Jul. 6, 2016  (JP) .................................. 2016-133959

(51) Int. Cl.
*A61B 5/15*       (2006.01)
*B01L 3/00*       (2006.01)
(Continued)

(52) U.S. Cl.
CPC .......... *G01N 1/38* (2013.01); *A61B 5/150022* (2013.01); *A61B 5/150343* (2013.01);
(Continued)

(58) Field of Classification Search
CPC ........ A61B 5/150022; A61B 5/150015; A61B 5/150007; A61B 5/15; A61B 5/150343;
(Continued)

(56) References Cited

U.S. PATENT DOCUMENTS 2,836,979 A    6/1958   Ryley
4,396,024 A    8/1983   Sarstedt
(Continued)

FOREIGN PATENT DOCUMENTS

CN    1439058 A    8/2003
CN    1906485 A    1/2007
(Continued)

OTHER PUBLICATIONS

Kyowa Medex Co., Ltd, WO 03/005039 A1, English Machine Translation, obtain by STIC at the USPTO, obtained on Jul. 29, 2019, pp. 1-69. (Year: 2019).*
(Continued)

*Primary Examiner* — Christine T Mui
(74) *Attorney, Agent, or Firm* — Sughrue Mion, PLLC

(57) ABSTRACT

An object is to provide a blood test kit and a blood analysis method capable of performing a blood test with a small amount of blood at high accuracy by visualizing a volume of blood collection and keeping the volume constant. Provided is a blood test kit for analyzing a concentration of a target component in a blood sample using a normal component homeostatically present in blood, the kit including: a blood collection instrument for collecting the blood sample; a diluent solution for diluting the collected blood sample; and a storing instrument for storing the diluted blood sample, in which the blood collection instrument is a capillary.

16 Claims, 4 Drawing Sheets

(51) Int. Cl.
  *G01N 1/38* (2006.01)
  *G01N 1/10* (2006.01)
  *G01N 33/96* (2006.01)
  *G01N 33/48* (2006.01)
  *G01N 33/49* (2006.01)

(52) U.S. Cl.
  CPC ........ *A61B 5/150755* (2013.01); *B01L 3/502* (2013.01); *G01N 1/10* (2013.01); *G01N 33/48* (2013.01); *G01N 33/491* (2013.01); *G01N 33/96* (2013.01); *A61B 5/150351* (2013.01); *B01L 2300/0838* (2013.01); *B01L 2300/12* (2013.01); *B01L 2300/161* (2013.01); *B01L 2400/0406* (2013.01)

(58) Field of Classification Search
  CPC ..... A61B 5/150755; B01L 3/502; B01L 3/50; B01L 3/00
  USPC .......................................... 436/179; 422/430
  See application file for complete search history.

(56) References Cited

U.S. PATENT DOCUMENTS

| | | | |
|---|---|---|---|
| 2001/0055784 | A1 | 12/2001 | Noda et al. |
| 2002/0153316 | A1 | 10/2002 | Nanba et al. |
| 2004/0043477 | A1 | 3/2004 | Schibli |
| 2004/0141888 | A1 | 7/2004 | Nanba et al. |
| 2004/0253658 | A1* | 12/2004 | Crouch .................. C12Q 1/485 435/15 |
| 2005/0232813 | A1 | 10/2005 | Karmali |
| 2008/0086042 | A1 | 4/2008 | Brister et al. |
| 2011/0020195 | A1* | 1/2011 | Luotola .............. A61B 10/0045 422/512 |
| 2011/0053289 | A1 | 3/2011 | Lowe et al. |
| 2012/0000299 | A1 | 1/2012 | Buechner |
| 2013/0116597 | A1* | 5/2013 | Rudge .............. A61B 5/150358 600/575 |
| 2016/0011150 | A1* | 1/2016 | Onuma ............ G01N 27/44791 204/451 |

FOREIGN PATENT DOCUMENTS

| | | |
|---|---|---|
| CN | 1969184 A | 5/2007 |
| CN | 101547633 A | 9/2009 |
| CN | 201926660 U | 8/2011 |
| CN | 102316989 A | 1/2012 |
| EP | 1 156 335 A3 | 12/2003 |
| JP | 59-180674 U | 12/1984 |
| JP | 10-221334 A | 8/1998 |
| JP | 2000-232972 A | 8/2000 |
| JP | 2001-330603 A | 11/2001 |
| JP | 3093189 U | 4/2003 |
| JP | 2003-161729 A | 6/2003 |
| JP | 2009-109196 A | 5/2009 |
| JP | 2009-122082 A | 6/2009 |
| JP | 2011-515171 A | 5/2011 |
| JP | 2011-112451 A | 6/2011 |
| JP | 2015-105936 A | 6/2015 |
| KR | 10-2007-0006904 A | 1/2007 |
| WO | WO 03/005039 A1 * | 1/2003 ............. G01N 33/72 |
| WO | 2011/065212 A1 | 6/2011 |
| WO | WO 2011/065212 A1 * | 6/2011 ............. G01N 33/49 |

OTHER PUBLICATIONS

Osawa et al, WO 2011/065212, English Machine Translation, obtained by STIC at the USPTO, obtained on Jul. 26, 2019, pp. 1-20. (Year: 2019).*
Office Action dated Jun. 18, 2019, from the European Patent Office in counterpart European application No. 16821432.8.
Communication dated Mar. 4, 2019, from the State Intellectual Property Office of People's Republic of China in counterpart Chinese Application No. 201680039443.9.
Communication dated Jan. 24, 2019 from European Patent Office in counterpart European Application No. 16 821 432.8.
Office Action dated Sep. 4, 2018, issued in corresponding Japanese Application No. 2016-133959, 4 pages in English and Japanese.
International Preliminary Report on Patentability dated Aug. 3, 2017 in PCT/JP2016/070008 [PCT/IPEA/409].
Written Opinion for PCT/JP2016/070008 dated Oct. 4, 2016 [PCT/ISA/237].
Masatoshi Horita, et al., "Establishment of Mail Medical Examination System Using Immediate Plasma Separating Device by the Self-Collection Blood—The Method of Dilution Ratio Calculation by Using Internal Standard for the Sample with Different Amount of Collecting Blood", The Japanese Journal of Clinical Pathology, Jul. 25, 2008, pp. 577-583 and p. 642, vol. 56, No. 7.
International Search Report for PCT/JP2016/070008 dated Oct. 4, 2016 [PCT/ISA/210].
Extended European Search Report dated Jun. 6, 2018, from the European Patent Office in counterpart European Application No. 16821432.8.
Office Action dated Jun. 24, 2019, issued by the Korean Intellectual Property Office in corresponding Korean Application No. 10-2018-7000469.
Office Action dated Sep. 27, 2019 from the State Intellectual Property Office of the P.R.C in Chinese application No. 201680039443.9.
Office Action dated Dec. 5, 2019, issued by the Korean Intellectual Property Office in corresponding Korean Application No. 10-2018-7000469.
Office Action dated Jan. 28, 2019, issued by the Korean Intellectual Property Office in Korean Application No. 10-2018-7000469.
Office Action dated Feb. 18, 2020 from the State Property Office of the P.R.C. in Chinese application No. 201680039443.9.

* cited by examiner

BLOOD TEST KIT AND ANALYZING METHOD USING THE SAME

CROSS-REFERENCE TO RELATED APPLICATIONS

This application is a Continuation of PCT International Application No. PCT/JP2016/070008 filed on Jul. 6, 2016, which claims priority under 35 U.S.C § 119(a) to Japanese Patent Application No. 2015-135066 filed on Jul. 6, 2015 and Japanese Patent Application No. 2016433959 filed on Jul. 6, 2016. Each of the above application(s) is hereby expressly incorporated by reference, in its entirety, into the present application.

BACKGROUND OF THE INVENTION

1. Field of the Invention

The present invention relates to a blood test kit for analyzing a target component in a blood sample and a method for analyzing blood using the same.

2. Description of the Related Art

As blood collection, generally, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a sealed state in a blood collection container, and tests are performed therein. In a case where the blood is transported without separating blood cells and blood plasma, tests are performed after a medical institution or a test institution performs centrifugation to separate the blood into blood cells and blood plasma. In addition, in the self-blood collection which is performed by a subject to be tested, the collected blood is separated into blood cells and blood plasma by a separation membrane, and the blood is transported to a test lab in a separated state, and then tests are performed therein.

JP2003-161729A discloses a method for testing a blood sample collected by self-blood collection, and specifically discloses a method for quantitatively determining a component to be quantitatively determined in a biological specimen, the method including 1) step of preparing a specimen for quantitation consisting of an unknown volume of a biological specimen containing a component to be quantitatively determined which is collected without quantitatively determining the volume thereof, and a certain volume of an aqueous solution containing a certain amount of an indicator substance, 2) step of obtaining a dilution factor (a) of the biological specimen from a concentration ($C_1$) of the indicator substance in the aqueous solution of a certain volume which contains a certain amount of the indicator substance, and a concentration ($C_2$) of the indicator substance in the specimen for quantitation, 3) step of obtaining a concentration (Y) of the component to be quantitatively determined in the specimen for quantitation, and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured, an amount of a normal component originally and homeostatically present in the sample, other than the target component, is measured, a volume of the sample is determined from the amount of this normal component and a known concentration of the normal component in the sample, and therefore a concentration of the target component to be analyzed in the sample is determined from the volume of the sample and the amount of the target component to be analyzed.

In addition, JP2009-122082A discloses that a small volume of blood is collected from a human or an animal using a blood dilution quantitative instrument, and after dilution of the blood, or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

Furthermore, JP1998-221334A (JP-H10-221334A) discloses a hemolysis measuring method characterized by measuring an antigen or an antibody, in which blood collected by using a blood collection tube of a small volume is diluted with a hemolytic diluent solution so as to hemolyze blood cell components, and then the diluted hemolytic specimen is added to an immunological measurement system.

Meanwhile, in a case where a subject to be tested collects a blood sample, blood is collected by using a lancet equipped with a small blade and is used for quantitatively determining a concentration of an arbitrary component in the blood, but generally, it is required to collect 100 µL or more of a blood sample.

SUMMARY OF THE INVENTION

In the method disclosed in JP2003-161729A, it is required that a ratio of a diluent solution to a blood sample volume is set high in a case of a small volume of a blood sample. In this case, a change rate in a volume of a diluent solution before and after diluting the blood sample becomes very small, and a change rate in a concentration of an internal standard substance becomes small, and therefore there is a problem that a level of repeatability and reproducibility with respect to measurement values decreases.

JP2001-330603A discloses that about 100 µL of whole blood of a healthy subject is added dropwise to a porous membrane, blood cells are separated to develop serum, and thereafter, 150 µL of a physiologically isotonic solution, PBS (phosphate-buffered saline: pH 7.4) is added thereto, and the supernatant obtained by centrifuging the obtained solution is analyzed as an analytical specimen, but does not disclose collection of blood of less than 100 µL.

In the method of JP2009-122082A, a blood volume of 10 µL is accurately collected with a micropipette so as to be analyzed, but in a case where the blood is collected by a patient who lacks experience in blood collection, it is difficult to accurately collect a certain volume thereof, and therefore a case in which tests are performed with blood collection including errors will result in measurement values including the errors.

The method disclosed in JP2009-109196A is the measurement with a dilution factor of about 10, and in a case where the dilution factor is further increased to sufficiently secure a volume of diluted blood, there is a problem that a level of repeatability and reproducibility with respect to measurement values decreases, as same as in JP2003-161729A.

As described above, the methods of JP2003-161729A to JP2009-109196A were not sufficient for performing the analysis at high accuracy in a case of using a small volume of blood sample. Meanwhile, blood collection is an invasive action that damages the skin, and depending on persons, there is a case of feeling uncomfortable staring at the red color of blood. Therefore, it is common to have desires for collecting the blood as soon as possible and stopping the blood flowing out from the wound. In accordance with such circumstances, the blood is not always collected in a constant volume and varies in many cases. The large variation in a volume of blood collection results in a deterioration of accuracy of a dilution factor, and therefore visualizing a volume of blood collection and keeping the volume constant are desired.

An object to be solved by the present invention is to provide a blood test kit and a blood analysis method capable of performing a blood test with a small amount of blood at high accuracy by visualizing a volume of blood collection and keeping the volume constant.

As a result of intensive studies to solve the object described above, the inventors of the present invention have found that the object described above can be solved by using a blood collection instrument having a shape of a capillary in a blood test kit which is for analyzing a concentration of a target component in a blood sample by using a normal component homeostatically present in blood, the kit including a blood collection instrument for collecting the blood sample; a diluent solution for diluting the collected blood sample; and a storing instrument for storing the diluted blood sample, and therefore have completed the present invention. According to the present invention, the following inventions are provided.

[1] A blood test kit for analyzing a concentration of a target component in a blood sample using a normal component homeostatically present in blood, the kit comprising: a blood collection instrument for collecting the blood sample; a diluent solution for diluting the collected blood sample; and a storing instrument for storing the diluted blood sample, in which the blood collection instrument is a capillary.

[2] A blood test kit for analyzing a concentration of a target component in a blood sample using a normal component homeostatically present in blood, the kit comprising: a blood collection instrument for collecting the blood sample; a diluent solution for diluting the collected blood sample; and a storing instrument for storing the diluted blood sample, in which the diluent solution contains a normal component not present in blood, and the blood collection instrument is a capillary.

[3] A blood test kit comprising: a blood collection instrument for collecting a blood sample; a diluent solution for diluting the collected blood sample, and which contains a normal component not present in blood; and a storing instrument for storing the diluted blood sample, in which the blood collection instrument is a capillary.

[4] The blood test kit according to any one of [1] to [3], in which the diluent solution does not contain the normal component homeostatically present in blood.

[5] The blood test kit according to any one of [1] to [4], further comprising: a separating instrument for separating and recovering blood plasma from the diluted blood sample.

[6] The blood test kit according to any one of [1] to [5], in which the capillary is marked with a graduation for checking a volume of the collected blood sample.

[7] The blood test kit according to any one of [1] to [6], in which the graduation is marked on a position indicating a lower limit of a volume range of the collected blood sample, the capillary has a stopper, and the stopper is provided for preventing the volume of the collected blood sample from exceeding an upper limit of the volume range of the blood sample to be collected.

[8] The blood test kit according to any one of [1] to [7], in which the capillary has a shape for collecting a predetermined volume of the blood sample.

[9] The blood test kit according to any one of [1] to [8], in which the capillary contains an anticoagulant therein.

[10] The blood test kit according to any one of [1] to [9], in which the capillary is made of a synthetic resin.

[11] The blood test kit according to [10], in which an inner wall of the capillary is hydrophilic-treated.

[12] The blood test kit according to [10] or [11], in which an end portion of the capillary on a side to aspirate a blood sample is tapered.

[13] The blood test kit according to any one of [10] to [12], in which the graduation is marked on at least one position of the capillary indicating a volume range of a blood sample to be collected, and an inner diameter of the capillary increases from a portion beyond the position of the graduation.

[14] The blood test kit according to any one of [10] to [12], in which the graduation is marked on at least one position of the capillary indicating a volume range of a blood sample to be collected, and the inner diameter of a portion including a position marked with the graduation of the capillary is smaller than those of other portions.

[15] The blood test kit according to any one of [10] to [14], in which a material constituting the capillary contains a component which absorbs at least some of light having a wavelength within a region of 600 nm or more.

[16] The blood test kit according to [1] or [2], in which the normal component which is homeostatically present in blood is sodium ions or chloride ions.

[17] The blood test kit according to [1] or [2], in which the normal component which is homeostatically present in blood is sodium ions or chloride ions, and another normal component which is homeostatically present in blood.

[18] The blood test kit according to [17], in which the other normal component is total protein or albumins.

[19] The blood test kit according to [17] or [18], in which analysis of a concentration of a target component in the blood sample is verified by using the other normal component.

[20] The blood test kit according to [2], in which the normal component not present in blood is lithium ions or glycerol 3-phosphate.

[21] The blood test kit according to [3], in which the normal component not present in blood is lithium ions or glycerol 3-phosphate.

[22] A method (excluding medical practice) for analyzing a concentration of a target component in a blood sample, the method comprising: using the blood test kit according to any one of [1] to [21].

An object of the present invention is to provide a blood test kit and a blood analysis method capable of performing a blood test with a small amount of blood at high accuracy by visualizing a volume of blood collection and keeping the volume constant.

DESCRIPTION OF THE PREFERRED EMBODIMENTS

Figure 1:
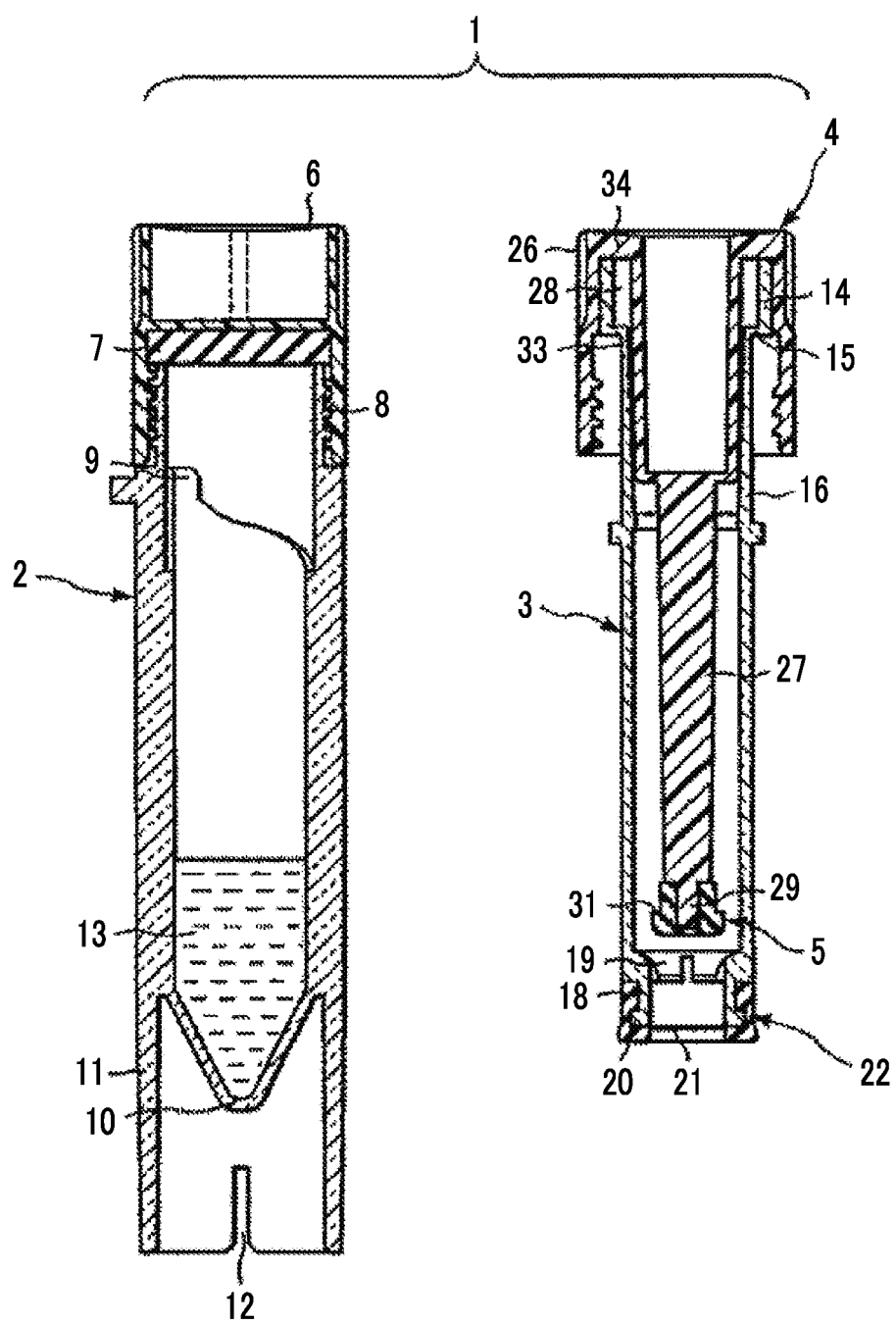
FIG. 1 illustrates an example of a configuration of a storing instrument for storing a diluted blood sample.

Hereinafter, an embodiment the present invention will be described. A range indicated by X to Y includes values of an upper limit X and a lower limit Y. A normal component homeostatically present in blood may be referred to as an external standard substance or an external standard. In addition, a normal component not present in blood may be referred to as an internal standard substance or an internal standard.

As a method of collecting a small volume of blood, a method of performing blood analysis using a filter paper is disclosed in JP1998-104226A (JP-H10-104226A), Furthermore, a method of using a porous material having a high level of blood retention property instead of a filter paper is disclosed in JP2001-330603A. In these methods, it is described that in order to extract blood components absorbed in the material with a buffer solution and the like and measure the components, sodium ions, chloride ions, calcium ions, protein, and the like which are external standard substances homeostatically present in the blood are used as a reference substance for estimating a dilution ratio by a buffer solution in a case where blood is eluted and redissolved. In these methods, a volume of blood collection varies, and if a dilution ratio of the collected blood becomes high, accuracy of analysis thereafter decreases, and thus the result varies. Because the blood is once coagulated and solidified, the stability of the target component to be analyzed is not sufficiently secured in some cases. In addition, as a buffer solution for extracting a biological component from a dried specimen, it is necessary to use a buffer solution to which NaOH, NaCl, or HCl is added in order to adjust the pH and stabilize the biological component. Therefore, there was a problem that concentrations of sodium ions and chloride ions which are present at a relatively high concentration, are homeostatic components in the specimen, and have little difference between individuals, cannot be used as an external standard, which is for correcting a concentration of another biological component of the diluted specimen.

Meanwhile, a method is disclosed in JP2003-161729A as a method for diluting a small volume of the collected blood with a buffer solution containing an internal standard and quantitatively determining an unknown amount of components present in the diluted blood plasma from a dilution factor of the internal standard substance. N-(2-hydroxy-3-sulfopropyl)-3,5-dimethoxyaniline sodium salt (HSDA) or acid blue 9 (brilliant blue FCF) is used as an internal standard substance, and a buffering agent and a preservative are used for stably maintaining blood. Such a formulation realized maintaining the stability of the components thereof by not coagulating the blood, but in a case where a volume of blood collection varies and a collection volume is small, there still were problems that a dilution ratio of an internal standard substance after dilution becomes small, and the reliability of test accuracy deteriorates as an amount of blood components itself decreased. In addition, in the method of diluting with a buffer solution, a biological component is stored in a buffer solution at physiological conditions of pH 7.4, and thus is excellent in stability during transportation, but because a specimen is added to a buffer solution to which an internal standard was added, a dilution ratio of the internal standard is small, and there is a problem that with addition of only a small amount of the specimen, a measurement error is likely to occur.

In examples of these related art, a phosphate buffered saline is used in a buffer solution for extraction because of excellence in maintaining the stability of a biological component, but the phosphate buffered saline contains sodium ions or chloride ions. Therefore, sodium ions or chloride ions cannot be used as an external standard, and calcium ions, proteins, and the like are used. Accordingly, in order to perform a blood test with a small volume of the blood at high accuracy, use of an external standard substance for correcting a dilution ratio disclosed in the related art and use of a buffer solution containing an internal standard substance disclosed in the related art were not sufficient for ensuring test accuracy.

Although being homeostatic substances in the blood, in sodium ions for example, a distribution width of a normal value is 134 to 146 mmol/L, and therefore it is necessary to more accurately calculate a dilution factor. A decrease of the accuracy of a dilution factor affects a bad influence on the test accuracy, and therefore a risk of deteriorating the reliability of a test increases. Particularly, in a case where there is only a little contamination due to an external standard substance eluted from a member constituting a kit into a buffer solution, if a volume of blood collection is large or small, a degree of influence of the contamination on calculation of a dilution factor varies. JP2001-330603A does not all mention about maintaining constant such a degree of influence of the contamination of an external standard substance eluted from a member constituting a kit into a buffer solution, on calculation of a dilution factor.

In addition, JP2003-161729A discloses about an internal standard, but does not disclose about the use of an external standard in combination. Accordingly, there is no disclosure regarding the contamination of the external standard, and a specific means for preventing the contamination is not proposed at all. Furthermore, in JP1998-221334A (JP-H10-221334A), it is disclosed that blood is collected using a capillary, but dilution is performed with a buffer solution containing NaCl, and use of an external standard is not disclosed.

An object of the present invention is to provide a blood test kit for performing analysis of a concentration of a target component by precisely determining a dilution factor, and a blood analysis method using the kit, in a method for analyzing a concentration of a target component by diluting a small volume of blood with a buffer solution. As a means for solving the above, an embodiment in which a volume of blood collection is maintained to be a constant value (at least equal to or larger than a minimum of an allowable volume of blood collection) by collecting blood using a capillary is employed. In addition, in a preferred embodiment, not only an external standard is used but also an internal standard is used.

In addition, in blood collection using a fiber rod (fiber) of the related art, it is difficult for a person who collects blood to check a volume of collected blood, and sample loss due to the fact that blood infiltrated into the fiber rod is not completely released into a buffer solution, that is, a factor causing a deterioration in test accuracy due to a small volume of blood collection, occurs. With respect to this, in the present invention, blood is collected using a capillary, and therefore it is possible to visually check a volume of a collected blood sample and to prevent the sample loss. A person who collects blood feels relief by the fact that a volume of a collected blood sample can be visually checked.

According to the present invention, in the method for analyzing a target component in a blood sample, it is possible that a volume of blood to be collected is easily maintained at a certain value, and that the volume thereof is at least equal to or larger than a desired volume range of a blood sample even in a case where a patient collects blood by himself. In addition, quantitation of a component to be analyzed can be performed at high accuracy by making the influence of an external standard substance eluted from a member constituting the kit into a buffer solution, on calculation of a dilution factor constant.

Furthermore, in the present invention, a capillary marked with a graduation is used as an embodiment, and thus a person who collects blood can check a volume of collected blood. Therefore, it is possible to relatively precisely estimate a dilution factor, and to estimate whether a calculated value of a dilution factor is appropriate based on a measurement result, at high accuracy. There are advantages that a person who collects blood can visually check that a volume of a collected blood sample is within an allowable range, and that the volume thereof satisfies at least a minimum volume, and therefore the person can transport a blood sample to a test institution while feeling relief. In addition, it is possible to check a volume of a collected blood sample by using the capillary marked with a graduation, and to provide information of the checked volume to the test institution together with the blood sample. The information provided can be used for checking whether a dilution factor is appropriately calculated in the test institution.

[Blood Test Kit]

A blood test kit of the present invention is for analyzing a concentration of a target component in a blood sample using a normal component homeostatically present in blood, and includes a blood collection instrument for collecting the blood sample; a diluent solution for diluting the collected blood sample; and a storing instrument for storing the diluted blood sample, in which the blood collection instrument is a capillary.

Analyzing of a concentration of a target component in a blood sample includes determining a concentration of a target component (that is, quantitatively determining a target component), determining whether a concentration of a target component is equal to or higher than a predetermined reference value or equal to or lower than a predetermined reference value, and the like, and an embodiment of the analysis is not particularly limited.

[Method for Blood Collection and Amount Thereof]

The blood test kit of the present invention is for collecting a blood sample so as to perform the analysis of a target component in the blood sample. The blood collection by using the blood test kit of the present invention may be carried out by a subject to be tested himself, or may be carried out by a qualified person such as a doctor.

In a preferred embodiment, a patient himself pricks a fingertip and the like using a blade-attached instrument such as a lancet and then collects the blood flowing out of the skin. It is preferable that the blood is collected in a manner of reducing the invasiveness so as to alleviate the burden on a patient, and when collecting the blood, it is desirable to be able to collect the blood with little pain or painlessly. In this case, it is desired that a depth and a size of the wound are small, by which a volume of blood that can be collected is very small. Accordingly, a volume of a sample collected by the blood test kit of the present invention (that is, a volume of the collected blood) is preferably 100 μL or less. In the present invention, even with such a small volume of blood collection, it is easy to maintain a blood collection volume to be a constant value, and it is possible to suppress a variation in a dilution factor to be calculated.

[Normal Component Homeostatically Present in Blood]

As above, in a method in which a target component after diluting blood plasma of which a dilution factor of blood plasma components is high, is obtained from a change rate of a concentration of a substance present in the diluent solution beforehand, in order to precisely analyze a concentration of blood plasma present in the blood before dilution, a change rate in concentration is extremely small, which leads to adverse effects that measurement error becomes high and reproducibility of measurement deteriorates. Accordingly, a preferred embodiment of the present invention is the blood test kit for analyzing a concentration of a target component in a blood sample by using a normal component which is homeostatically present in blood.

The phrase "by using" a normal component means that a dilution factor for analyzing a concentration of a target component is determined based on a normal value (homeostatic value) of the normal component. Accordingly, the analysis of a concentration of a target component of a blood sample by using a normal component homeostatically present in blood also means that a concentration of a target component is analyzed by determining a dilution factor based on a normal value (homeostatic value) of the normal component homeostatically present in blood.

Examples of the normal component which is homeostatically present in the blood include sodium ions, chloride ions, potassium ions, magnesium ions, calcium ions, total protein, albumins, and the like. As a concentration of these normal components contained in serum and blood plasma of the blood sample, a concentration of sodium ions is 134 to 146 mmol/L (average value: 142 mmol/L), a concentration of chloride ions is 97 to 107 mmol/L (average value: 102 mmol/L), a concentration of potassium ions is 3.2 to 4.8 mmol/L (average value: 4.0 mmol/L), a concentration of magnesium ions is 0.75 to 1.0 mmol/L (average value: 0.9 mmol/L), a concentration of calcium ions is 4.2 to 5.1 mmol/L (average value: 4.65 mmol/L), a concentration of total protein is 6.7 to 8.3 g/100 mL (average value: 7.5 g/100 mL), and a concentration of albumins is 4.1 to 5.1 g/100 mL (average value: 4.6 g/100 mL). The present invention is for enabling measurement of a target component in a case where a volume of blood to be collected is extremely small for alleviating patient's pain. In a case where a small volume of blood is diluted with a diluent solution, it is required that a concentration of "the normal component homeostatically present in the blood", which is present in the diluent solution is accurately measured. As a dilution factor becomes high, a concentration of a component, which is originally present in the blood, in the diluent solution decreases, and depending on a dilution factor, there is a possibility that measurement error is included when measuring the concentration. Accordingly, it is preferable to measure the normal component present at a high concentration in a small volume of the blood so as to detect the normal component at sufficiently high accuracy when a small volume of the blood components is diluted at a high dilution factor. In the present invention, it is preferable to use sodium ions ($Na^+$) or chloride ions ($Cl^-$) which are present at a high concentration among the components homeostatically present in the blood sample. Furthermore, it is most preferable to measure sodium ions which are present in the blood at a highest amount among the normal components homeostatically present in the blood described above. Regarding sodium ions, an average value represents a normal value (median value of the reference range), and this value is 142 mmol/L, accounting for 90 mole % or more of total cations in the blood plasma.

[Normal Component Not Present in Blood]

The preferred embodiment of the present invention is the blood test kit for analyzing a concentration of a target component in a blood sample by using a normal component not present in blood. Such a test kit may be a kit for using a normal component not present in blood together with a normal component homeostatically present in blood, and may be a kit for only using a normal component not present in blood and not using a normal component homeostatically present in blood.

In both cases, it is possible to use the normal component not present in blood by adding a predetermined concentration of the normal component in the diluent solution. As the normal component not present in blood, it is possible to use a substance which is not contained in the blood sample at all, or is contained thereto but in an ultra-small amount. As the normal component not present in blood, it is preferable to use substances which do not interfere with the measurement of the target component in the blood sample, substances which do not decompose under the action of biological enzymes in the blood sample, substances which are stable during dilution, substances which do not pass through a blood cell membrane and not contained in the blood cells, substances which are not adsorbed to a storing container of the diluent solution, and substances which can be utilized by a detection system capable of measurement at high accuracy.

As the normal component not present in blood, a substance which is stable even if the substance is stored for a long period of time in a state of being added to the diluent solution, is preferable. Examples of the normal component not present in blood include glycerol 3-phosphate, Li, Rb, Cs, or Fr as alkali metal, and Sr, Ba, or Ra as alkaline earth metal, and Li and glycerol 3-phosphate is preferable.

These normal components not present in blood can develop color by adding a second reagent at the time of measuring a concentration after blood dilution, and the concentration in the diluted blood can be obtained from color optical density. For example, regarding the measurement of lithium ions added to the diluent solution, a large number of specimens of a small amount can be easily measured by the chelate colorimetric method (halogenated porphyrin chelating method: perfluoro-5,10,15,20-tetraphenyl-21H,23H-porphyrin) using an automatic biochemistry analyzer.

[Diluent Solution]

The blood test kit of the present invention includes the diluent solution for diluting a collected blood sample. In a case where the kit is for analyzing a concentration of a target component in a blood sample by using a normal component homeostatically present in blood, the diluent solution does not contain a normal component homeostatically present in blood. The phrase "does not contain" in the present specification means that the solution "substantially does not contain" the component. The phrase "substantially does not contain" means that the solution does not contain a homeostatic substance used for obtaining a dilution factor at all, or even if the homeostatic substance is contained, this means a case where an ultra-small amount of concentration is contained to the extent that does not affect measurement of a homeostatic substance in a diluent solution after diluting a blood sample. In a case where sodium ions or chloride ions are used as a normal component homeostatically present in blood, a diluent solution which substantially does not contain sodium ions or chloride ions is used as a diluent solution.

A pH of blood is generally maintained constant at a pH of about 7.30 to 7.40 for healthy subjects. Accordingly, in order to prevent degradation or denaturation of a target component, a diluent solution is preferably a buffer solution having a buffering action within a pH range of pH 6.5 to pH 8.0, preferably pH 7.0 to pH 7.5, and further preferably pH 7.3 to pH 7.4, and the diluting solution is preferably a buffer solution containing a buffering component for suppressing variation in pH.

In the related art, as the type of the buffer solution, an acetate buffer solution (Na), a phosphate buffer solution (Na), a citrate buffer solution (Na), a borate buffer solution (Na), a tartrate buffer solution (Na), a Tris (tris(hydroxymethyl) aminoethane buffer solution (Cl), a HEPES ([2-[4-(2-hydroxyethyl)-1-piperazinyl]ethanesulfonic acid]) buffer solution, a phosphate buffered saline (Na), and the like are known. Among these, as a buffer solution having a pH around 7.0 to 8.0, the phosphate buffer solution, the Tris buffer solution, and the HEPES buffer solution are representative. However, the phosphate buffer solution contains a sodium salt of phosphoric acid, the Tris buffer solution has a dissociation pKa of 8.08, and thus is usually used in combination with hydrochloric acid for imparting buffering ability around pH 7.0 to pH 8.0, and a dissociation pKa of sulfonic acid of HEPES is 7.55, but in order to adjust buffer solution at constant ionic strength, a HEPES mixture of sodium hydroxide and sodium chloride is used. Therefore, these solutions are useful as a buffer solution having an action of maintaining pH constant, but contain sodium ions or chloride ions which are substances preferably used as an external standard substance in the present invention, and thus, application thereof to the present invention is not preferable in a case where the kit is for analyzing a concentration of a target component in a blood sample by using a normal component homeostatically present in blood.

In a case where the kit is for analyzing a concentration of a target component in a blood sample by using a normal component homeostatically present in blood, it is preferable that a buffer solution to be used does not contain sodium ions or chloride ions (the meaning of the phrase "does not contain" is as described above). Such a buffer solution is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid (pKa=7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable. In addition, pKa represents an acid dissociation constant.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of the chelating agent include ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, suppress degradation of biological components by bacteria, and stabilize the biological components.

In addition, the buffer solution contains a normal component not present in blood in the kit for analyzing a target component using a normal component not present in blood. It is import that an internal standard substance to be described below is not contained, and a measuring system for blood analysis is not interfered therewith.

From the viewpoint of diluting whole blood, by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent homolysis. The osmotic pressure can be adjusted to be isotonic by measurement of a target component, salts which do not affect a normal component homeostatically present in the blood, sugars, buffering agents, and the like. The osmotic pressure of the buffer solution can be measured by an osmometer.

[Volume of Diluent Solution and Dilution Factor]

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various components in the blood such as ALT (alanine transaminase), AST (aspartate aminotransferase), γ-GTP γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is important that a certain volume thereof is secured. In consideration of reducing the invasiveness as much as possible at the time of collecting blood, it is desirable to avoid that a volume of blood collection becomes 100 µL or more, and thus a dilution factor becomes 7 or higher.

[Capillary]

The kit of the present invention employs a capillary as a blood collection instrument. In a case where, for example, glycerol 3-phosphate is used as an internal standard substance in a diluent solution in a method of quantitatively analyzing a component by diluting a small volume of blood sample with the diluent solution, a dilution factor can be calculated at high accuracy if there is a sufficient volume, specifically about 100 µL, of the blood sample. In addition, in a case where a dilution factor is calculated using an external standard substance, the dilution factor becomes high as a volume of blood is small, and it is easily affected by contamination of the external standard substance eluted from the member of the kit during dilution, and therefore measurement accuracy of the quantitative analysis decreases. The present inventors have conducted intensive studies on a means for obtaining a test result of which accuracy is high by using a volume of blood collection not exceeding 100 µL for example and suppressing the influence of the contamination of the external standard substance eluted from the member into the diluent solution, in a case of analyzing a concentration of a component by diluting a blood sample of a small volume with the diluent solution. As a result, it was found that it is optimal to collect a volume of blood collection at a constant value by using the capillary as a blood collection instrument.

Hereinafter, embodiments of the capillary according to the present invention will be described with reference to examples shown in the drawings.

[Structure of Capillary]

Figure 2:
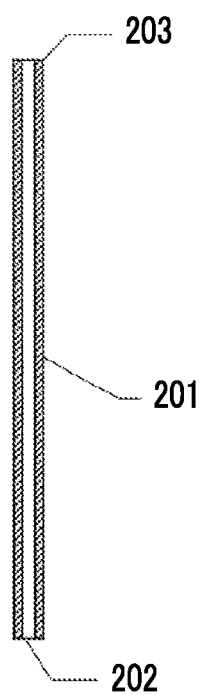
FIG. 2 illustrates a cross sectional diagram of an example of a capillary.

FIG. 2 illustrates a cross sectional diagram of an example of the capillary according to the present invention. The capillary is usually a tube made of a narrow tubular main body 201 having an approximately constant inner diameter. In a case where one of both ends 202 and 203 thereof is brought into contact with blood, blood can be collected inside the capillary by a capillary phenomenon (a phenomenon in which a liquid penetrates into the capillary against gravity). When an appropriate amount of blood is sucked up, the other end of the capillary blood collection instrument is sealed by stopping with a finger or the like, and the suction is stopped. Next, the capillary holding the blood sample inside is carried to the storing instrument storing the diluent solution for diluting the blood sample, in a state being stopped at the end with the finger. After holding one end of the capillary in the storing instrument, the blood sample is stored in the storing instrument by releasing the finger stopping the end. The capillary may be sealed using a sealer such as a cap, silicone putty, and paraffin resin, clay, and the like, instead of sealing by stopping with a finger.

The inner diameter of the capillary is preferably 0.5 to 2.0 mm in consideration of a size of blood cells, the occurrence of the capillary phenomenon, and the like. A length of the capillary is preferably 5 to 15 cm in consideration of ease of handling and the like, and is more preferably 5 to 10 cm because it is desirable that the capillary is compact in consideration of constituting the blood test kit. For example, regarding a volume of blood which can be collected by the capillary in a case where the inner diameter is 1.1 mm to 1.2 mm and the length is 7.5 cm, 70 µL of blood can be collected.

[Gradation and Capillary with Stopper]

Figure 3:
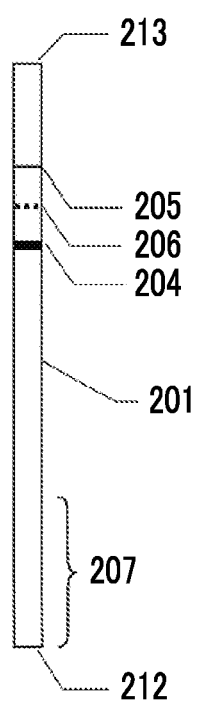
FIG. 3 illustrates an example of a shape of the capillary and positions of graduations.

FIG. 3 is an example of the capillary marked with a graduation for checking a volume of a collected blood sample. A maximum volume of the blood sample that can be collected by the capillary is theoretically a volume that fills the inside of the capillary at once, but the capillary can be marked with a lower limit gradation 204 and an upper limit gradation 205 on a position indicating a lower limit and a position indicating an upper limit of a volume range of the blood sample to be collected, by which it is possible to determine whether a volume of the collected blood sample is appropriate or not. For example, in a case where it is preferable that a blood sample is collected at about 65 μL, the gradation may be marked on the position of 55 μL and 75 μL which are ±10 μL. It is obvious that the graduation (central gradation 206) may be marked on the central value of 65 μL, but it is preferable to mark graduations with different appearances so as not to mistake the gradation indicating the lower limit or the upper limit. A volume range of the blood sample to be collected is a volume range of the blood sample that is allowable for analyzing a target component contained in the blood sample at high accuracy, and in the above example, the range is within 55 to 75 μL.

An inner diameter of a portion including the position marked with the gradation of the capillary may be smaller than that of the other portions. This is because if there is a gradation on a part with a small inner diameter, that is, a narrow part of a tube, a volume can be collected more accurately. In addition, this is because by decreasing the inner diameter, a rising speed of blood within the capillary is increased, and therefore timing of sealing is easy to take.

A lower limit gradation 204 marked on the position indicating the lower limit affects the test accuracy if the gradation is below the lower limit, and therefore it is preferable that the gradation line is are thick and easy to see. By making the capillary asymmetric above and below, a person who collects blood can also reduce the risk of mistaking a blood contact end 212 for contacting the blood of the capillary with a sealing end 213 which is the other end. On the other hand, blood collection exceeding the upper limit is in a direction to further suppress the influence of the contamination of the external standard substance from the part, but the variation tends to increase as compared to a case where a volume of blood collection close to the lower limit. In order to ensure that a volume of collected blood is not equal to or lower than the upper limit, for example, a stopper with a hole is provided inside time position indicating the upper limit of the capillary (for example, the upper limit gradation 205 in FIG. 3), and when blood reaches the stopper, the suction may be stopped by sealing the upper end of the capillary with a finger or the like. By using the stopper, even if the sealing timing with the fingers or the like is slightly shifted, the suction speed of the blood is suppressed, and it is possible to more reliably collect the blood of a volume equal to or lower than the upper limit. In addition, a person who collects blood can be confused if a plurality of graduations are marked, and therefore it is also preferable to provide only the stopper with a hole without marking the graduation on the capillary.

Furthermore, the inner diameter of the end 212 on a side to be brought into contact with the blood of the capillary may be made smaller than that of the other parts. This makes it easier for the capillary phenomenon to occur. At this time, an end portion 207 on the side to be brought into contact with the blood of the capillary may be tapered such that the inner diameter becomes smaller toward the end.

[Example of Shape of Capillary]

Figure 4:
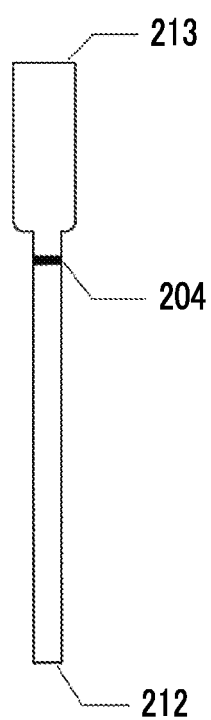
FIG. 4 illustrates an example of a shape of the capillary and a position of the graduation.

Furthermore, the capillary can have a shape for collecting a predetermined volume of a blood sample. An example of such a capillary is designed to have a predetermined volume such that the inside is filled with the blood sample at once. In another example, in a case where a predetermined volume of a blood sample is collected, the capillary has a shape so that blood cannot be collected any more. Specifically, for example, the capillary is a capillary in which the inner diameter is rapidly increased from a certain position of the capillary (for example, the inner diameter is made to exceed 2 mm) so that the capillary phenomenon is unlikely to occur if blood exceeds that position, as shown in FIG. 4. Alternatively, by minimizing the inner diameter from a certain position of the capillary, the change in volume with respect to the graduation misalignment is reduced, and the measurement accuracy can be enhanced. The capillary having such a shape may be marked with a gradation on the position indicating the upper limit or the position indicating the lower limit of a volume of blood to be collected. The position at which the inner diameter is changed can be a position marked with a graduation or a position beyond the gradation, but in a case of increasing the inner diameter, the latter is preferable. This is because if there is the graduation on a narrow portion of the tube beyond the position where the inner diameter becomes larger, a volume can be accurately determined. The position beyond the gradation means a position indicating an increased volume by 1 μL to 7 μL, preferably 3 μL to 5 μL, from a volume in a case where blood is collected up to the gradation.

[Anticoagulant-Containing Capillary]

In the capillary used in the present invention, it is preferable that an anticoagulant is contained in the capillary in a case where blood obtained by puncturing with a lancet and the like is collected directly with the capillary. Examples of such a capillary include a capillary in which an anticoagulant such as heparin and EDTA salt is applied to the inner surface of the capillary. As the anticoagulant, various substances can be used, but in a case where an external standard is used for analysis, those which do not substantially contain the external standard are selected.

[Synthetic Resin Capillary]

The capillary used in the present invention may be made from glass or synthetic resin. Furthermore, a capillary made from another material may be coated with the synthetic resin. In the present specification, plastic is used synonymously with the synthetic resin. It is preferable that the capillary is made from plastic from the viewpoint of safety that breakage is less likely to occur than the capillary made from glass. Examples thereof include polyethylene, polypropylene, polyvinyl chloride, polyvinylidene chloride, polystyrene, polyvinyl acetate, polyurethane, acrylonitrile butadiene styrene resin (ABS resin), acrylonitrile styrene resin (AS resin), acrylic resin (PMMA), polycarbonate, silicone resin, and the like.

In a case where the capillary is made from glass, since the water contact angle of the glass is 10 degrees or less, the inner wall of the capillary has sufficient hydrophilicity as it is, and therefore the capillary phenomenon of the capillary is fully exhibited and blood can be collected quickly. On the other hand, in a case where the capillary is made from plastic, the water contact angle of polycarbonate is 85 degrees and the water contact angle of acrylic is 70 degrees, for example. In order to quickly collect blood, it is preferable that the inner wall of the capillary is hydrophilic-treated. As a hydrophilic treatment, hydrophilization by plasma treatment is possible, for example.

It is also preferable that the capillary is made from plastic from the viewpoint that it is easy to perform a process of making the end portion to be brought into contact with blood into a tapered shape as described above and a process to change the inner diameter of the capillary.

[Colored Capillary]

There are some people having resistance to staring at the red color of blood in a case of using the capillary in the self-blood collection. In general, a capillary for collecting blood used by medical staff and researchers is transparent, but one of the preferred embodiments of the capillary used in the present invention is a capillary colored such that the red color of blood is inconspicuous. If the capillary is made from plastic, coloring is easy. Alternatively, glasses and the like using a transmission medium capable of shielding an absorption wavelength region of hemoglobin in blood, such that the collected blood shows a color other than red while the capillary itself is transparent, may be used as a constituting component of the blood test kit.

On the other hand, although hemoglobin associated with oxygen seems to be red, it is difficult to absorb abruptly from a wavelength of 600 nm toward a longer wavelength side. Thus, for example, by using a filter that absorbs wavelengths longer than 680 nm, the red color of the blood can be made inconspicuous (such that the color looks like an orange color).

[Separating Instrument for Separating and Recovering Blood Plasma from Diluted Blood Sample]

There is a possibility that a blood sample collected by the kit of the present invention is left alone for a long period of time in a diluted state before performing the analysis. During the time, for example, red blood cells are hemolyzed, which leads to the release of substances, enzymes, and the like which are present in the blood cells into the blood plasma or serum, and therefore a test result is affected thereby. Furthermore, there is a possibility that an absorption amount of the released hemoglobin affects a case of measuring an amount of a component to be analyzed with light information such as the optical absorption of the component to be analyzed, and the like. Therefore, it is preferable that the hemolysis is prevented. Accordingly, an embodiment in which the kit includes a separating instrument for separating and recovering blood plasma from a diluted blood sample is preferable. A preferred example of the separating instrument is a separation membrane. It is possible to use the separation membrane such that blood cells are separated and blood plasma components are recovered by applying pressure on the diluted blood sample, trapping the blood cell components with the separation membrane, and allowing the blood plasma components to pass through the separation membrane. In this case, it is preferable that an anticoagulant is used. In addition, in order to ensure accuracy of measurement, it is preferable that backflow of the blood plasma passed through the separation membrane to the blood cells side does not occur. Therefore, specifically, the kit can include a backflow prevention means described in JP2003-270239.A as a constituent component.

The kit of the present invention is capable of realizing a method in which a target component to be analyzed can be analyzed at high measurement accuracy even with a volume of blood collection of 100 μL or less, and is preferably a kit including an instruction manual in which information that measurement can be accurately performed even with a small volume of blood collection of 100 μL or less, to which position of the capillary blood is to be collected, and the like is described for a patient.

[Specific Example of Kit]

In one preferred embodiment, the kit includes, in addition to the capillary, the diluent solution, the first storing instrument in which the diluent solution is stored (which also may be a storing instrument for storing a diluted blood sample), the separating instrument for separating and recovering blood plasma from a blood sample diluted with the diluent solution, the holding instrument for holding the separating instrument, the second storing instrument for storing the recovered blood plasma, and the sealing instrument for keeping the stored blood plasma in the second storing instrument. As specific examples of the instruments other than the capillary, it is possible to use instruments described in FIG. 1 to FIG. 13 of JP3597827B. FIG. 1 of JP3597827B is incorporated as FIG. 1 of the present application.

A blood separating instrument 1 includes a blood collection container 2 (storing instrument in which a diluent solution is stored, which may be referred to as the first storing instrument in some cases. This is a storing instrument for storing a diluted blood sample), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, art upper end opening portion of the blood collection container 2 is sealed by a cap 6 via a packing 7, as shown in FIG. 1. The storing instrument for storing a diluted blood sample of the present invention corresponds to a combination of the blood collection container 2 and the tubular body 3 in the configuration of FIG. 1. That is, the storing instrument for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separating instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and the sealing lid 5 is detachably provided on the lower end portion 29 (refer to FIG. 1). The sealing lid 5 is made of silicone rubber.

Specifically, the operation of separating and recovering blood plasma from a blood sample is performed as below. The blood collected by the capillary is added to the blood collection container 2 storing the diluent solution, and then the blood and the diluent solution are thoroughly shaken to be mixed while noting that bubbles are not generated by holding an upper portion of the blood collection container 2. Next, the tubular body 3 holding the filtration membrane 21 (for preventing solution leakage due to infiltration into a side surface of a cylinder at the time of separating blood plasma from blood cells) is inserted into the blood collection container 2 such that the filtration membrane faces downward, and the filtration membrane is slowly pushed into the bottom of the blood collection container 2 at a constant speed. At this time, the blood plasma passes through the filtration membrane of the tubular body 3 and then floats on the upper portion, and the blood cells remains on the lower portion of the blood collection container 2. Thereafter, the cap piston 4 is slowly pushed into the tubular body 3, by which mixing of the blood plasma with the blood cells due to backflow is prevented by the sealing lid 5.

A method for separating blood by the instruments described above is described in detail in paragraphs 0023 to 0026 and FIG. 12 and FIG. 13 of JP3597827B, the contents of which are incorporated in the present specification.

The number of various components contained in the blood test kit of the present invention is not particularly limited, and each component may be one, or there may be a plurality of, for example, 2 or more thereof.

The material of the part, other than the capillary, included in the blood test kit of the present invention is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, and the like.

The blood test kit of the present invention can provide the capillary, the diluent solution for diluting a blood sample, the storing instrument for storing the diluted blood sample, and if desired, the arbitrary component described above in a manner of being stored in the storing container for storing these members.

Method for Analyzing Blood

The present invention further provides a blood analysis method in which the kit of the configuration described in [1] of the present specification is used. The blood analysis method includes an aspect which is a medical practice (practice performed by a doctor) for humans and an aspect which is not a medical practice for humans (for example, an aspect in which a person who performs blood collection is a patient himself and an analyzer is a person other than a doctor, an aspect for non-human animals, and the like). The blood analysis method of the present invention may be performed by the self-blood collection in which a subject to be tested collects blood by himself, or may be performed by the general blood collection in which a qualified person such as a doctor collects blood using a syringe. As a preferred embodiment, a patient pricks the fingertip and the like by himself using an instrument equipped with a small blade such as a lancet, and then collects blood flowing out of the skin.

In the present invention, a biological specimen which is a target to be analyzed is blood, and the blood is a concept of including serum or blood plasma. Preferably, it is possible to use blood plasma or serum obtained by collecting a small volume of blood by a subject to be tested, diluting the blood with a buffer solution, and then separating blood cells through a filter or by centrifugation.

As a component of the blood sample, a blood plasma component separated from a blood sample by a separation means is preferable.

The origin of a blood sample is not limited to humans, and may be mammals, birds, fish, and the like which are animals other than humans (non-human animals). Examples of the animals other than humans include horses, cows, pigs, sheep, goats, dogs, cats, mice, bears, pandas, and the like. The origin of a biological specimen is preferably humans.

As an embodiment of the blood analysis method of the present invention, the analysis of a concentration of a target component is performed by using a normal component homeostatically present in the blood sample. Regarding the normal component homeostatically present in the blood sample, the same explanation in [1] applies thereto.

An occupancy rate of blood plasma components in the blood of a subject to be tested is about 55% in terms of a volume ratio, but the ratio varies depending on changes in salt intake of the subject, and the like. Therefore, in the present invention, a dilution factor of blood plasma is calculated by using a normal value of the normal component which is homeostatically present in the blood plasma, and a concentration of a target component in the blood plasma of a blood sample is analyzed by using the calculated dilution factor. As a method for calculating a dilution factor, it is possible to obtain a dilution factor by calculating a dilution factor (Y/X) of the blood plasma components in a blood sample from a measurement value (concentration X) of an external standard substance (for example, sodium ions and the like) in a diluent solution of the blood plasma, and a known concentration value (concentration Y; in a case of sodium ions, 142 mmol/L) of the external standard substance (for example, sodium ions and the like) contained in the blood plasma of the blood sample. Using this dilution factor, a value (concentration Z) of a target component in a diluent solution of the blood plasma is measured, and by multiplying this measurement value by the dilution factor, it is possible to measure a concentration $[Z \times (Y/X)]$ of a target component to be analyzed actually contained in the blood plasma of the blood sample.

A concentration of sodium ions can be measured by, for example, the flame photometric method, the glass-electrode method, the titration method, the ion selective electrode method, the enzyme activity method, and the like. In a particularly preferred aspect, the enzyme activity method utilizing that β-galactosidase is activated by sodium ions, which is that a concentration of sodium ions in a specimen diluted with the diluent solution and β-galactosidase activity are in a proportional relationship is employed for the measurement of sodium ions.

In addition, in order to confirm whether the blood test kit in which an amount of a normal component derived from the member is defined is actually used, or whether a method for diluting blood and recovering blood plasma is normally performed, it is preferable that an additional dilution factor is separately obtained from the other normal component in blood plasma to check whether values thereof match with the dilution factor obtained above. The term "match" means, with respect to two measurement values (a, b), a ratio of their differences to their average values, that is, $|a-b|/\{(a+b)/2\} \times 100$ is 20% or smaller, preferably 10% or smaller, and more preferably 5% or smaller. Accordingly, it is possible to verify that the analysis of a concentration of a target component of a blood sample is normally performed. Examples of the normal component homeostatically present in the blood plasma, which is other than sodium ions and chloride ions are preferably selected from total protein or albumins, and it is more preferable that the component is total protein. Examples of a method for measuring total protein include the known method such as the biuret method, the ultraviolet absorption method, the Bradford method, the Lowry method, the bicinchoninic acid (BCA) method, and the fluorescence method, and it is possible to select a method to be used appropriately depending on characteristics, sensitivity, specimen amount, and the like of a measurement specimen.

As a second embodiment of the blood analysis method of the present invention, the analysis of a concentration of a target component is performed by using a normal component not present in blood. In this case, a blood test kit including a diluent solution which contains a normal component not present in blood is used.

As a third embodiment of the blood analysis method of the present invention, the analysis of a concentration of a target component is performed by using a normal component homeostatically present in blood and a normal component not present in blood. Using the two normal components in combination, it is possible to realize the analysis method having higher reliability.

In this case, sodium ions are used as a normal component homeostatically present in blood and lithium ions are used as a normal component not present in blood, and in a case where sodium ions measurement is carried out by the enzyme activity method (to be described later) utilizing that β-galactosidase activity is in a proportional relationship, and lithium ions measurement is carried out by a chelate colorimetric method (to be described later), a dilution factor of the blood sample can be calculated by any one of Formulas 1 to 4.

$X=(A+C)/(B+D)$   Formula 1:

$X=\{(A^2+C^2)^{1/2}\}/\{(B^2+D^2)^{1/2}\}$   Formula 2:

$X=a\times(B+D)\pm b$   Formula 3:

(a and b are coefficients, and a standard curve represented by Formula 3 is prepared in advance by acquiring data of (B+D) and a dilution factor)

$X=A/B'$ $(B'=(A\times D)/C)$   Formula 4:

In the above formulas, A, B, C, D, B', and X are defined as follows.
A: Absorbance in a case of coloring a buffer solution
B: Absorbance change after adding blood plasma
C: Absorbance at a median value of 142 mmol/L of blood plasma sodium
D: Absorbance at a concentration of sodium ions after diluting blood plasma
B': Correction value of an absorbance of a normal component not present in the blood of diluted blood plasma obtained by a dilution factor calculated from an absorbance of blood plasma sodium
X: Dilution factor of blood plasma As another calculation method for a case of obtaining a dilution ratio, an aspect in which a dilution ratio is calculated by Formula 5 using the root-mean-square method, a concentration of a target component to be analyzed in a diluent solution is multiplied by the dilution ratio calculated by Formula 5, and therefore a concentration of a target component in the components of a blood sample is analyzed, is preferable.

Formula 5:

$X=[\{(A/B)^2+(C/D)^2\}/2]^{1/2}$   (1)

A concentration of a target component in the components of the blood sample can be calculated from a concentration of a target component of the diluent solution based on the above dilution factor.

The target component to be analyzed is not limited and any substance contained in a biological specimen is a target. Examples thereof include biochemical test items in blood used for clinical diagnosis, markers of various diseases such as tumor markers and hepatitis markers, and the like, and include proteins, sugars, lipids, low molecular weight compounds, and the like. In addition, not only a concentration of a substance is measured, but also an activity of a substance having an activity such as an enzyme is targeted. Measurement of each target component can be carried out by a known method.

In a case of measuring sodium ions, it is possible to use an enzymatic assay by which sodium ions in several μL of specimen of very low sodium concentration (24 mmol/L or less) diluted with a diluent solution are measured by utilizing that the enzyme activity of the enzyme galactosidase is activated by sodium ions. This method can be applied to a biochemical/automated immunoassay analyzer, and is highly efficient and economical for not required of another measuring instrument for sodium ions measurement.

The present invention will be described by the following examples, but the present invention is not limited by the examples.

EXAMPLE

Reference Example 1

1. Preparation of Diluent Solution which Small Volume of Blood Specimen is Diluted After informed consent was obtained from a volunteer patient, blood of 7 mL collected from the vein by a syringe was obtained in a blood collection tube. From this collected blood, 80 μL and 60 μL were precisely weighed 10 times respectively with a capillary having an inner diameter of 1 mm. In addition, blood was aspirated ten times with a fiber rod on a distal end of a blood aspirator until the whole fiber rod stained red. Each was mixed with 360 μL of Diluent Solution 1 prepared as described below. A filter was used to separate blood cell components, and by using the diluted blood plasma as a specimen, each concentration of a biological component was measured with an automatic biochemistry analyzer.

(Composition of Diluent Solution)

A diluent solution was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

HEPES 50 mmol/L
2-amino-2-methyl-1-propanol (AMP) 50 mmol/L
D-Mannitol 284 mmol/L
Lithium chloride 1 mmol/L
EDTA-2K 0.8 mmol/L
PALP (pyridoxal phosphate) 0.05 mmol/L
Thiabendazole 0.0001% by mass
Amikacin sulfate 0.0003% by mass
Kanamycin sulfate 0.0005% by mass
Meropenem trihydrate 0.0005% by mass
Osmotic pressure 355 mOsm/kg
pH 7.4

2. Measurement of Concentration of Sodium Ions

A concentration of sodium ions was measured with respect to each diluent solution prepared in 1. The measurement was carried out by the enzyme activity method utilizing that β-galactosidase is activated by sodium ions, which is that each concentration of sodium ions in the diluent solution and β-galactosidase activity are in a proportional relationship. Specifically, after diluting the dilution solution of the blood five times by using purified water not containing sodium ions, 3 μL was weighed, 52 μL of a first reagent prepared as described below was added thereto, and then heated at 37° C. for 5 minutes. 26 μL of a second reagent prepared as described below was added thereto, and the change in absorbance was obtained by measuring an absorbance during 1 minute at a main wavelength of 410 nm and a complementary wavelength of 658 run by using JCA-BM6050-type automatic biochemistry analyzer (manufactured by JEOL, Ltd.). The concentration of sodium ions was measured from a calibration curve prepared in advance.

(Preparation of Reagent for Measuring Sodium Ions)

A reagent for measuring sodium ions having the following composition was prepared.

First Reagent
HEPES/LiOH (pH 8.0) 100 mmol/L
D-Mannitol 60 mmol/L,
N-acetylcysteine 30 mmol/L
Magnesium sulfate 1.52 mmol/L
β-galactosidase 1.1 kU/L
TRITON X-100 0.05% by mass Second Reagent
HEPES/LiOH (pH 8.0) 100 mmol/L
o-Nitrophenyl β-D-Galactopyranoside 15 mmol/L

3. Measurement of Dilution Factor of Blood Plasma Using Concentration of Sodium Ions A dilution ratio (Y/X) of each diluent solution was obtained from a concentration of sodium ions (X) in the diluent solution obtained as above, and a normal value (Y) of a concentration of sodium ions in blood plasma of the blood. An average value of the dilution ratios, and CV (coefficient of variation) (%), a coefficient of variation, which is a measure of the variation with respect to 10 specimens prepared with the capillary respectively from 80 μL and 60 μL of the collected blood, and 10 specimens prepared with the fiber rod respectively from the collected blood were obtained. The results are shown in Table 1.

diluent solution described above was carried out by the chelate colorimetric method (halogenated porphyrin chelating method: perfluoro-5,10,15,20-tetraphenyl-21H,23H-porphyrin). Specifically, after diluting the dilution solution of the blood 4.5 times by using purified water not containing lithium ions, 5 μL was weighed, 55 μL, of a third reagent prepared to have compositions described below was added thereto, and then heated at 37° C. for 10 minutes. An absorbance was measured at a main wavelength of 545 nm and a complementary wavelength of 596 nm by using JCA-BM6050-type automatic biochemistry analyzer (manufactured by JEOL Ltd.). The concentration of lithium ions was measured from a calibration curve prepared in advance.

(Preparation of Reagent for Measuring Lithium Ions)

A reagent for measuring lithium ions having the following composition was prepared.

Third Reagent
Perfluoro-5,10,15,20-tetraphenyl-21H,23H-porphyrin 0.05% by mass
Dimethyl sulfoxide 5% by mass
Triethanolamine 2% by mass
Polyethylene glycol-t-octylphenyl ether 2% by mass
Sodium dodecyl sulfate:2% by mass (Measurement of Dilution Factor)

A method for obtaining a dilution factor of blood plasma in blood and a calculation formula with respect to the result of a concentration of sodium ions previously obtained, the diluent solution prepared to have the composition of the diluent solution described above, and the diluted blood plasma obtained by diluting a small volume of a blood specimen prepared above, are shown in below.

A: Absorbance in a case of coloring the diluent solution at the time of measuring lithium ions B: Absorbance change measured at the time of measuring a concentration of lithium ions in the diluted blood plasma C: Absorbance at a median value of 142 mmol/L of blood plasma sodium D: Absorbance at a concentration of sodium ions after diluting blood plasma with the diluent solution X: Dilution factor of blood plasma

TABLE 1

| Volume of collected blood (μL) | Weighing Method | Diluent Solution 1 (μL) | Dilution factor (average value of 10-time measurements) | CV (%) of dilution factor (10-time measurements) | Notes |
|---|---|---|---|---|---|
| 80 μL | Capillary | 360 | 9.7 | 2.4 | Example |
| 60 μL | Capillary | 360 | 11.9 | 2.5 | Example |
| (Unclear) | Fiber rod | 360 | 10.2 | 10.5 | Comparative example |

4. Measurement of Dilution Factor of Blood Plasma Using Concentration of Sodium Ions and Concentration of Lithium Ions (Measurement of Lithium Ions in Diluent Solution)

A concentration of lithium ions in each diluent solution prepared in Reference Example 1 was measured as below.

Measurement of a concentration of lithium ions added to the diluent solution prepared to have the compositions of the For obtaining a dilution factor from blood plasma of a buffer solution, a relationship in Formula (1) was used.

$$X = [\{(A/B)^2 + (C/D)^2\}/2]^{1/2} \qquad (1)$$

Using Formula (1), an average value of the dilution ratios, and CV (%), a coefficient of variation, which is a measure of the variation with respect to each diluent solution of blood plasma prepared in 1 were obtained. The results are shown in Table 2.

TABLE 2

| Volume of collected blood (μL) | Weighing Method | Diluent Solution 1 (μL) | Dilution factor (average value of 10-time measurements) | CV (%) of dilution factor (10-time measurements) | Notes |
| --- | --- | --- | --- | --- | --- |
| 80 μL | Capillary | 360 | 9.2 | 2.0 | Example |
| 60 μL | Capillary | 360 | 11.9 | 2.2 | Example |
| — | Fiber rod | 360 | 10.2 | 7.2 | Comparative example |

5. Measurement of Dilution Factor of Blood Plasma Using Concentration of Lithium Ions With respect to the diluent solution prepared to have the compositions of the diluent solution described above, and the diluted blood plasma obtained by diluting the blood specimen of a small volume prepared as above, a dilution ratio of each diluent solution B/(B−A)] was obtained from a concentration of lithium ions (A) in the diluent solution after diluting the blood sample prepared in 4, and a concentration of lithium ions (B) in the diluent solution before diluting blood, and therefore an average value of the dilution ratios of the specimens, and CV (%), a coefficient of variation, which is a measure of the variation were obtained. The results are shown in Table 3.

TABLE 3

| Volume of collected blood (μL) | Weighing Method | Diluent Solution 1 (μL) | Dilution factor (average value of 10-time measurements) | CV (%) of dilution factor (10-time measurements) | Notes |
| --- | --- | --- | --- | --- | --- |
| 80 μL | Capillary | 360 | 9.1 | 2.6 | Example |
| 60 μL | Capillary | 360 | 11.9 | 2.7 | Example |
| — | Fiber rod | 360 | 10.3 | 10.8 | Comparative example |

Based on the results of Table 1, Table 2, and Table 3, it was found that by using the capillary marked with the graduation in a case where sodium ions which are components homeostatically present in blood are used as a standard substance, a level of repeatability and reproducibility with respect to a measurement value of a dilution factor becomes very high compared to a case in which blood is collected using a fiber rod, and that a level of repeatability and reproducibility becomes very high in a case where lithium ions which are internal standard substances are used. Therefore, it was found that the capillary is excellent in consideration of the ease of use and low cost in a case of being used in the blood test kit. Furthermore, by using sodium ions which are components homeostatically present in blood as a standard substance, and using, in combination, lithium ions contained in the diluent solution which substantially does not contain sodium ions as a standard substance, the excellent result of which a level of repeatability and reproducibility with respect to a measurement value of a dilution factor becomes further high is obtained, and therefore the same conclusion is obtained. Based on the conclusion, it was found that a concentration of a target component in a blood sample can be calculated and obtained at high accuracy.

Reference Example 2

Using the capillary, 80 μL of blood prepared in Reference Example 1 was weighed, and a concentration of total protein was measured with respect to the diluted specimen of blood plasma which was mixed with the diluent solution and in which blood cell components were separated through a filter, by a method described below.

(Measurement of Concentration of Total Protein in Diluted Sample of Blood Plasma)

Measurement using the biuret method as the measurement principle was performed. Biuret reagent: 3.0 mmol/L, copper sulfate 400 μl, potassium sodium tartrate 21.3 mmol/L. and MOH 0.75 mmol/L were prepared and mixed with the diluted blood plasma. After mixing, the mixture was left alone at 37° C. for 10 minutes, and it was Waited until a complex exhibiting blue-violet color of 540 to 560 nm due to protein and copper ions in blood plasma was formed under an alkaline environment, the absorbance was measured at 545 nm, and therefore, a concentration of total protein in the diluted blood plasma after separating blood cells was quantitatively determined using a calibration curve obtained from the absorbance of a standard solution.

The same values were obtained with respect to the average value of the dilution factors obtained from the concentration of total protein, and the average value of the dilution factors obtained from the concentration of sodium ions prepared in Reference Example 1. Based on the result, it was found that the verification that the measurement of the dilution factor obtained from the concentration of sodium ions was performed normally is possible.

EXPLANATION OF REFERENCES

1: blood separating instrument
2: blood collection container
3: tubular body
4: cap piston
5: sealing lid
6: cap
7: packing
8: screw portion
9: locking portion
10: bottom portion
11: leg portion
12: slit grooves
13: diluent solution
14: expanded diameter section 15: thin wall portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion
201: tubular main body
202: end
203: end
204: lower limit gradation
205: upper limit gradation
206: central gradation
207: end portion
217: blood contact end
213: sealing end

What is claimed is:

1. A blood test kit for analyzing a concentration of a target component in a blood sample, the kit comprising:
 a blood collection instrument for collecting the blood sample;
 a buffer solution that does not contain sodium ions for diluting the collected blood sample; and
 a storing instrument for storing the diluted blood sample,
 wherein the blood collection instrument is a capillary inside which the blood sample can be collected by a capillary phenomenon,
 the capillary has a shape for collecting a predetermined volume of the blood sample, in which the inner diameter of the capillary is rapidly increased from a certain position so that the capillary phenomenon is unlikely to occur if the collected blood exceeds that position, and
 the buffer solution contains a normal component not present in blood, and the normal component not present in blood is lithium ions.

2. The blood test kit according to claim 1, further comprising:
 a separating instrument for separating and recovering blood plasma from the diluted blood sample.

3. The blood test kit according to claim 1,
 wherein the capillary is marked with a graduation for checking a volume of the collected blood sample.

4. The blood test kit according to claim 3,
 wherein the graduation is marked on a position indicating a lower limit of a volume range of the collected blood sample,
 the capillary has a stopper, and
 the stopper is provided for preventing the volume of the collected blood sample from exceeding an upper limit of the volume range of the blood sample to be collected.

5. The blood test kit according to claim 1,
 wherein the capillary contains an anticoagulant therein.

6. The blood test kit according to claim 1,
 wherein the capillary is made of a synthetic resin.

7. The blood test kit according to claim 6,
 wherein an inner wall of the capillary is hydrophilic-treated.

8. The blood test kit according to claim 6,
 wherein an end portion of the capillary on a side to aspirate a blood sample is tapered.

9. The blood test kit according to claim 6,
 wherein the graduation is marked on at least one position of the capillary indicating a volume range of a blood sample to be collected, and
 an inner diameter of the capillary increases from a portion beyond the position of the graduation.

10. The blood test kit according to claim 7,
 wherein the graduation is marked on at least one position of the capillary indicating a volume range of a blood sample to be collected, and
 the inner diameter of a portion including a position marked with the graduation of the capillary is smaller than those of other portions.

11. The blood test kit according to claim 7,
 wherein a material constituting the capillary contains a component which absorbs at least some of light having a wavelength within a region of 600 nm or more.

12. A method for analyzing a concentration of a target component in a blood sample using the blood test kit according to claim 1, the method comprising:
 collecting the blood sample by the blood collecting instrument;
 diluting the collected blood sample with the buffer solution that does not contain sodium ions;
 storing the diluted blood sample in the storing instrument, and
 analyzing a concentration of the target component in the blood sample based on a concentration of a normal component homeostatically present in blood,
 wherein the buffer solution contains a normal component not present in blood, and the normal component not present in blood is lithium ions.

13. The method according to claim 12, wherein the normal component homeostatically present in blood is sodium ions or chloride ions.

14. The method according to claim 12, wherein the normal component homeostatically present in blood is sodium ions or chloride ions, and another normal component homeostatically present in blood.

15. The blood test kit according to claim 14, wherein the another normal component is total protein or albumins.

16. The blood test kit according to claim 12, the method further comprising verifying the analyzed concentration of the target component in the blood sample by using the another normal component.

* * * * *